(12) United States Patent
Buckland (10) Patent No.: US 10,518,293 B2
(45) Date of Patent: Dec. 31, 2019

(54) THICKNESS-PLANAR MODE TRANSDUCERS AND RELATED DEVICES

(71) Applicant: Sensus USA, Inc., Morrisville, NC (US)

(72) Inventor: Justin Rorke Buckland, Cambridge (GB)

(73) Assignee: Sensus USA, Inc., Morrisville, NC (US)

(*) Notice: Subject to any disclaimer, the term of this patent is extended or adjusted under 35 U.S.C. 154(b) by 423 days.

(21) Appl. No.: 15/374,129

(22) Filed: Dec. 9, 2016

(65) Prior Publication Data

US 2018/0161814 A1 Jun. 14, 2018

(51) Int. Cl.
*B06B 1/06* (2006.01)
*G01F 1/66* (2006.01)
*H01L 41/18* (2006.01)

(52) U.S. Cl.
CPC ............. *B06B 1/067* (2013.01); *G01F 1/667* (2013.01); *H01L 41/18* (2013.01)

(58) Field of Classification Search
CPC ..... B06B 1/067; B06B 1/0644; B06B 1/0662; H01L 41/047; H01L 41/18; G01F 1/662; G01F 1/667
See application file for complete search history.

(56) References Cited

U.S. PATENT DOCUMENTS

| | | | | |
|---|---|---|---|---|
| 4,404,489 A * | 9/1983 | Larson, III | ............... | H01L 41/29 174/254 |
| 4,523,122 A | 6/1985 | Tone et al. | | |
| 4,583,018 A * | 4/1986 | Izumi | .................... | B06B 1/0644 310/334 |
| 5,295,487 A * | 3/1994 | Saitoh | ....................... | B06B 1/06 310/334 |
| 5,743,855 A * | 4/1998 | Hanafy | ................. | B06B 1/0622 600/459 |
| 6,396,199 B1 * | 5/2002 | Douglas | ................ | B06B 1/0622 310/334 |
| 6,989,625 B2 | 1/2006 | Suzuki et al. | | |
| 2001/0021807 A1 * | 9/2001 | Saito | ....................... | B06B 1/067 600/437 |
| 2005/0061076 A1 | 3/2005 | Kim | | |

(Continued)

FOREIGN PATENT DOCUMENTS

| EP | 1 237 148 A2 | 9/2002 |
|---|---|---|
| WO | WO 2007/064214 A2 | 6/2007 |

OTHER PUBLICATIONS

Gomez Alvarez-Arenas et al., "Novel Impedance Matching Materials and Strategies for Air-Coupled Piezoelectric Transducers," IEEE Sensors, 2013, 4 pages.

(Continued)

*Primary Examiner* — J. San Martin
(74) *Attorney, Agent, or Firm* — Stanek Lemon Crouse & Meeks PA (57) ABSTRACT

Transducers are provided including a piezoelectric block having first and second opposing surfaces; a first conductive flexible support layer on the first surface of the piezoelectric block, the first flexible support layer having a first thickness; and a second flexible support layer on the second surface of the piezoelectric block, the second flexible support layer having a second thickness. Related devices are also provided.

23 Claims, 4 Drawing Sheets

(56) References Cited

U.S. PATENT DOCUMENTS

| | | | |
|---|---|---|---|
| 2005/0156491 A1 | 7/2005 | Scott | |
| 2014/0375171 A1* | 12/2014 | Tai | H01L 41/0825 |
| | | | 310/341 |
| 2018/0242066 A1* | 8/2018 | Buckland | H04R 1/06 |

OTHER PUBLICATIONS

Gomez Alvarez-Arenas, Tomas E., "A Nondestructive Integrity Test for Membrane Filters Based on Air-Coupled Ultrasonic Spectroscopy," IEEE Transactions on Ultrasonics, Ferroelectrics, and Frequency Control, vol. 50, No. 6, Jun. 2003, pp. 676-685.

Gomez Alvarez-Arenas, Tomas E., "Acoustic Impedance Matching of Piezoelectric Transducers to the Air," IEEE Transactions on Ultrasonics, Ferroelectrics, and Frequency Control, vol. 51, No. 5, May 2004, pp. 624-633.

Percin et al. "Piezoelectrically actuated flextensional micromachined ultrasound transducers," Ultrasonics, vol. 40, 2002, pp. 441-448.

Piezoelectric Tonpilz Transducer, Consol Application Gallery, Prior Art, Printed from the Internet at https://www.comsol.com/model/piezoelectric-tonpilz-tranducers-11478; 52 pages.

Notification of Transmittal of the International Search Report and the Written Opinion of the International Searching Authority, or the Declaration, PCT/US2017/065026, dated Feb. 12, 2018.

Notification Concerning Transmittal of International Preliminary Report on Patentability, PCT/US2017/065026, dated Jun. 20, 2019, 10 pages.

* cited by examiner

THICKNESS-PLANAR MODE TRANSDUCERS AND RELATED DEVICES

CROSS REFERENCE TO RELATED APPLICATIONS

This application is related to U.S. application Ser. No. 15/374,044, filed Dec. 9, 2016 entitled Thickness Mode Transducers and Related Devices and Methods, the disclosure of which is hereby incorporated herein by reference as if set forth in its entirety.

FIELD

The present inventive concept relates generally to transducers and, more particularly, to ultrasonic transducers and related methods and devices.

BACKGROUND

Ultrasonic transducers preferably include small but precisely dimensioned piezoelectric blocks in order to provide a high degree of part-to-part repeatability with low material costs. Conventional devices generally include a cylindrical piezoelectric block having a thickness that defines a resonant frequency of the piezoelectric block. In these devices, the element thickness may be, for example, about 7.0 mm when operated at 170 kHz and about 3.0 mm when operated at 400 kHz. However, fabricating precisely dimensioned piezoelectric cylinders of this size and shape can be very expensive as the cylinder faces have to be machined after firing.

Furthermore, conventional devices generally provide an electrical connection to the piezoelectric block using a soldered wire. However, solder can be unreliable and may cause increased part-to-part variability as the mass and placement of solder is not tightly controlled and can have a significant effect on the transducer vibrational behavior. As the size of the piezoelectric block decreases, these problems generally become more severe.

SUMMARY

Some embodiments of the present inventive concept provide transducers including a piezoelectric block having first and second opposing surfaces; a first conductive flexible support layer on the first surface of the piezoelectric block, the first flexible support layer having a first thickness; and a second flexible support layer on the second surface of the piezoelectric block, the second flexible support layer having a second thickness.

In further embodiments, the first and second thicknesses may be substantially the same and may be substantially less than a thickness of the piezoelectric block.

In still further embodiments, the first and second conductive flexible support layers may include thin metal sheets of material. The thin metal sheets of material may include stainless steel sheets of material.

In some embodiments, the first and second conductive flexible support layers may be flexible circuits with a copper trace.

In further embodiments, the first and second conductive flexible support layers may have a thickness of from about 0.025 mm to about 0.1 mm.

In still further embodiments, the piezoelectric block may include a soft PZT material selected from one of grade P5A material and P5H material.

In some embodiments, the piezoelectric block may have a thickness of from about 0.5 mm to about 5.0 mm.

In further embodiments, the resonant frequency of the transducer may be about 400 kHz and dimensions of the first and second conductive flexible support layers may be 4.2×4.2×0.1 mm; and dimensions of the piezoelectric block may be 4×4×2 mm.

In still further embodiments, the first and second conductive flexible support layers may be coupled to the first and second surfaces of the piezoelectric block, respectively, using an adhesive.

In some embodiments, an electrical contact between the piezoelectric block and the first and second conductive flexible support layers may be obtained using the adhesive and without a wire soldered between the piezoelectric block and the first and second conductive flexible support layers.

In further embodiments, the transducer may further include an acoustic matching layer on one of a gas and liquid facing surface of one of the first and second conductive flexible support layers.

In still further embodiments, the transducer may be an ultrasonic transducer configured for one of a gas meter, a water meter and a heat meter.

Some embodiments of the present inventive concept provide an electronic device including at least one transducer. The at least one transducer includes a piezoelectric block having first and second opposing surfaces; a first electrically conductive flexible support layer on the first surface of the piezoelectric block, the first electrically conductive flexible support layer having a first thickness; and a second electrically conductive flexible support layer on the second surface of the piezoelectric block, the second electrically conductive flexible support layer having a second thickness.

BRIEF DESCRIPTION OF THE DRAWINGS

FIGS. 3 and 4 are contour plots illustrating results of axisymmetric transducer simulations, plotting axial velocity (m/s) at the centre of the transducer; FIG. 3 illustrates varying of the piezoelectric thickness (y_pzt), radius (r_face)=2.3 mm (ref: A) and FIG. 4 illustrates varying radius, and piezoelectric thickness=2 mm (ref: B).

DETAILED DESCRIPTION

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed in the background of the inventive concept, conventional cylindrical piezoelectric blocks may be expensive to manufacture and soldering the electrical connections may provide poor transducer performance. A dicing saw may be used to address the difficult and costly manufacturing of a cylindrical piezoelectric element. The dicing saw may be used to create a cuboid piezoelectric element instead of a cylindrical piezoelectric element, which can be a cost-effective way to create a precisely dimensioned part. However, this generally requires a thickness of less than approximately 2.5 mm. As a result, there is a need for a transducer design where the piezoelectric element dimensions are small enough to be manufactured cost-effectively by dicing a piezoelectric tile with a wafer dicing saw.

A thickness mode ultrasonic transducer manufactured using a reduced volume of piezoelectric material to reduce manufacturing costs may be provided as discussed in commonly assigned U.S. patent application Ser. No. 15/374,044, the contents of which are hereby incorporated herein by reference as if set forth in its entirety. The piezoelectric element may be circular, or preferably cuboid to allow precise fabrication using a wafer dicing saw. Additional non-piezoelectric layers or parts may be used to reduce the thickness of piezoelectric material given a target operating frequency and to increase the acoustically transmitting area, however, this may increase the part count and number of adhesive bonding steps, both of which may be undesirable.

Accordingly, some embodiments of the present inventive concept provide a transducer including a piezoelectric element between electrically conductive flexible support layers, for example, thin flexible shims, which provide mechanical mounting as well as electrical connection. The light flexible electrically conducting structures may provide mechanical support and electrical contact to the piezoelectric element and possibly gas or liquid sealing for the transducer as will be discussed further herein with respect to FIGS. 1 through 7.

Figure 1:
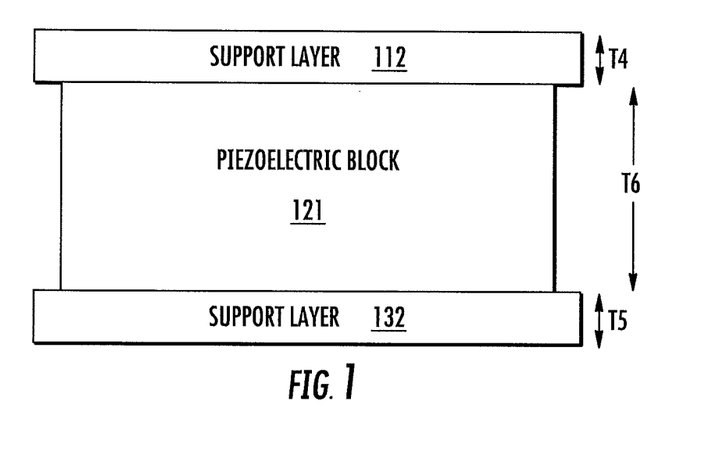
FIG. 1 is a block diagram illustrating transducers including electrically conductive flexible support layers according to some embodiments of the present inventive concept.

Referring now to FIG. 1, a transducer including electrically conductive flexible support layers in accordance with some embodiments of the present inventive concept will be discussed. As illustrated therein, a transducer 100 includes a piezoelectric block 121 and first and second conductive flexible support layers 112 and 122, respectively. The piezoelectric materials of the piezoelectric block 121 may be, for example, PZT, grades P5A and P5H or substantial equivalents thereof. However, it will be understood that embodiments of the present inventive concept are not limited to this configuration. In particular, embodiments of the present inventive concept are not limited to lead zirconate titanate (PZT) formulations and may extend to other piezoelectric ceramics without departing from the scope of the present inventive concept. In some embodiments, the piezoelectric block 121 may have a thickness T6 of from about 0.5 mm to about 5.0 mm. In some embodiments, the piezoelectric block 121 may have a thickness T6 of about 2.0 mm. The piezoelectric block may be circular, or it may be cuboid in shape to allow precise fabrication using a wafer dicing saw without departing from the scope of the present inventive concept.

The conductive flexible support layers 112 and 132 may be any flexible material that has the capability of providing an electrical contact. For example, in some embodiments, the flexible support layers may be provided by thin metal shims 112 and 132, for example, stainless steel shims, but could be other materials without departing from the scope of the present inventive concept. If metal shims are used, the shims should have a low mass and stiffness relative to the piezoelectric block. Providing stainless steel (metal shims) provides an electrically conductive material to the flexible piezoelectric compound. In some embodiments, the flexible support layers may be a flexible circuit material with a conductive trace, for example, copper without departing from the scope of the present inventive concept.

In some embodiments, the flexible support layers 112 and 132 may have thicknesses T4 and T5, respectively, of from about 0.025 mm to about 0.1 mm. The thicknesses T4 and T5 of the flexible support layers may be the same or different. In some embodiments of the present inventive concept, the thicknesses of the flexible support layer 112 and 132 are substantially the same. It should be understood that the thicknesses T4 and T5 of the flexible support layers are very small relative to the thickness of the piezoelectric block 121. In particular, the flexible support layers should be light and flexible compared to the piezoelectric block to provide mechanical support and electrical connection without greatly influencing the vibrational behavior of the piezoelectric block.

Figure 2A:
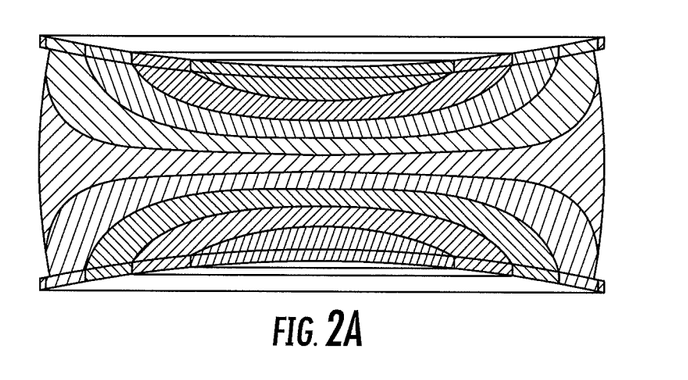
FIGS. 2A and 2B are diagrams illustrating thickness-planar mode transducers including metal shims in accordance with some embodiments of the present inventive concept.
Figure 2B:
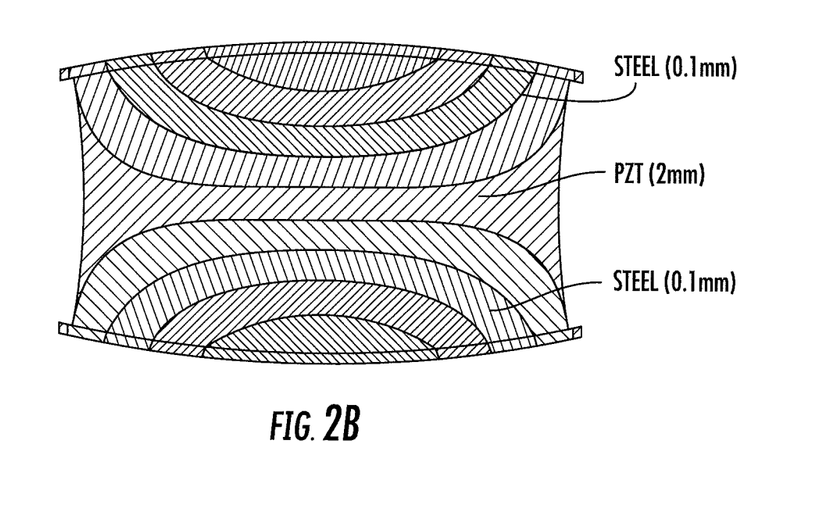

Referring now to FIGS. 2A and 2B, diagrams illustrating axial displacement of a 400 kHz thickness-planar mode transducer in accordance with some embodiments of the present inventive concept will be discussed. The 400 kHz thickness-planar mode transducer, like FIG. 1, includes a piezoelectric element having thin metal shims positioned on first and second surfaces of the piezoelectric element. The shims provide mechanical mounting and electrical connection. The piezoelectric dimensions in the example illustrated in FIGS. 2A and 2B are approximately 4×2×2 mm. As further illustrated, in this example, the piezoelectric element has a thickness of about 2.0 mm and the shims have a thickness of about 0.1 mm. As illustrated in FIG. 2A the transducer experiences compression and in FIG. 2B the transducer experiences expansion.

Finite element simulations were carried out using Ansys Multiphysics. An axisymmetric model was used, containing a piezoelectric centre region enclosed between upper and lower stainless steel sheets (0.1 mm thick). The harmonic response was simulated for a 10 Vpp drive, with frequency swept from 10 kHz to 1 MHz. A 5 percent damping factor was applied.

Figure 3:
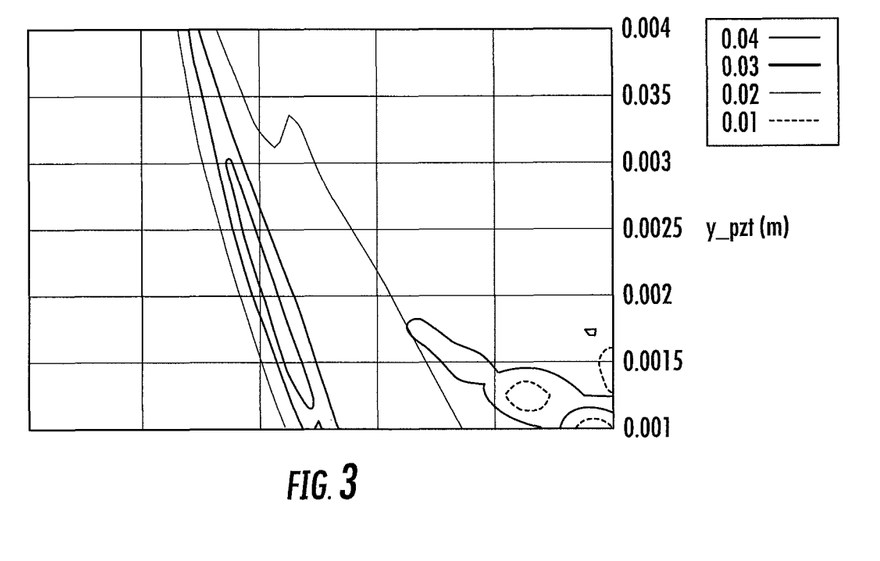
Figure 4:
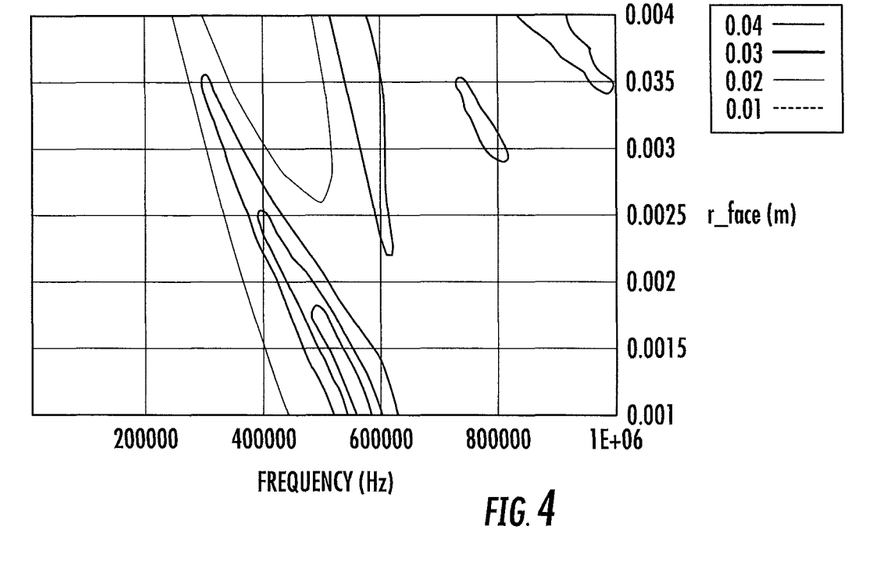

FIGS. 3 and 4 illustrate contour plots showing results of axisymmetric transducer simulations, plotting axial velocity (m/s) at the centre of the transducer. FIG. 3 illustrates results when the piezoelectric thickness (y_pzt) is varies and the radius (r_face) of 2.3 mm (ref: A). FIG. 4 illustrates a varying radius (r_face) and a PZT thickness of 2 mm (ref: B). The contour plots if FIGS. 3 and 4 indicate desirable combinations of operating frequencies and transducer dimensions. FIG. 3 illustrates an optimal operating frequency of about 400 kHz when the piezoelectric element thickness, y_pzt, is 2.0 mm. FIG. 4 illustrates an optimal operating frequency of approximately 400 kHz when the radius of the front face, r_face, is 2.5 mm. The operating frequency varies with both thickness and radius of the transducer, indicating the coupled thickness-planar nature of the resonant mode.

Figure 5:
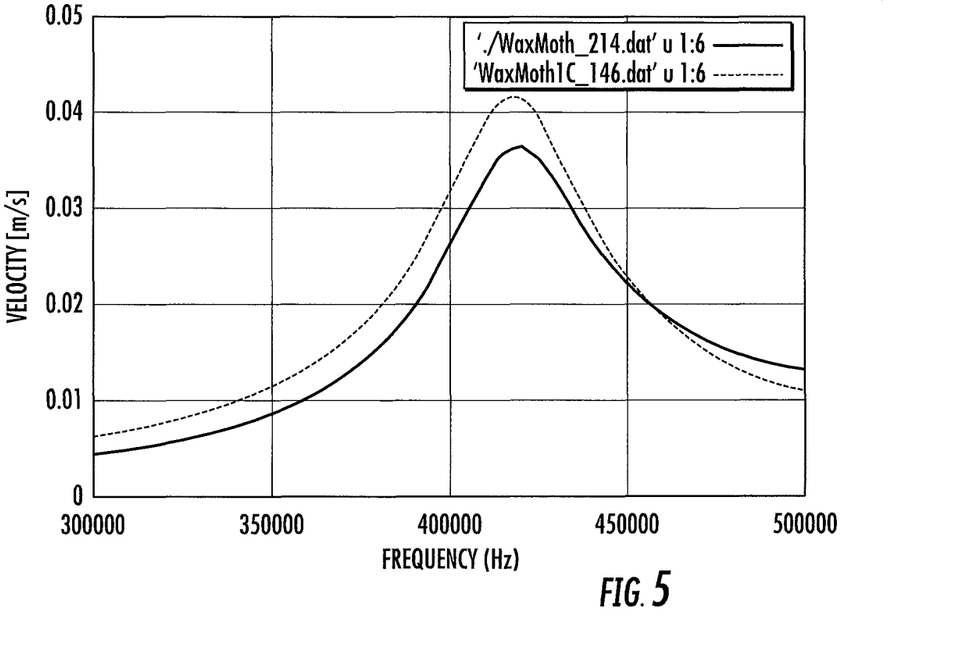
FIG. 5 is a graph comparing the axial velocities of embodiments of the present inventive concept illustrated in FIG. 1 and embodiments discussed in a related application incorporated by reference herein.

Referring now to FIG. 5, the simulated axial velocities of a transducer discussed in U.S. patent application Ser. No. 15/374,044 incorporated by reference above and the transducer illustrated in FIG. 1 are compared on the graph. As illustrated, the simulated axial velocity of the FIG. 1 transducer (lower trace) is slightly lower than the axial velocity of the other transducer (upper trace). Although the velocity of the FIG. 1 transducer is slightly lower, this slight loss in velocity may be a small disadvantage compared to the ease of manufacturing of the device of FIG. 1. In other words, the flexible support layers are easier to manufacture in the device of FIG. 1 than the front and back blocks of the other transducer. A further advantage of embodiments of the present inventive concept is that the flexible support layers provide mechanical mounting, electrical connection and optionally, liquid or gas sealing functions, possibly eliminating the need for additional parts in the transducer assembly.

Figure 7:
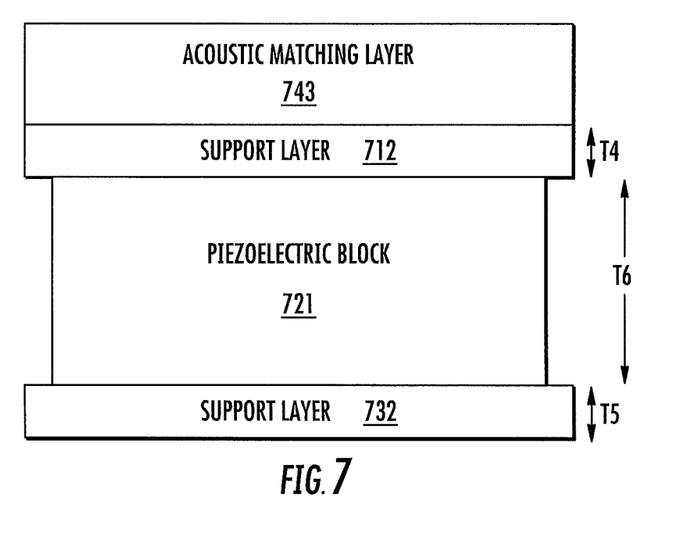
FIG. 7 is a diagram illustrating a transducer including an acoustic matching layer in accordance with some embodiments of the present inventive concept.

As illustrated in FIG. 7, some embodiments of the present inventive concept may include an acoustic matching layer on one of a gas and liquid facing surface of one of the first and second conductive flexible support layers. Although the acoustic matching layer 743 is illustrated as being positioned on support layer 712, embodiments of the present inventive concept are not limited to this configuration. The acoustic matching layer could be positioned on support layer 732 without departing from the scope of the present inventive concept.

The acoustic matching layers are used to improve acoustic transmission efficiency between a high acoustic impedance acoustic element (PZT, impedance $Z_1$) and a low acoustic impedance medium (gas, impedance $Z_3$). The acoustic impedance of a material is defined as the product of density and speed of sound.

In the case of a single matching layer, the ideal matching layer acoustic impedance, $Z_2$, is the geometric mean of the transducer and gas acoustic impedances:

$$Z_2 = \sqrt{Z_1 Z_3} \qquad \text{Eqn. (1)}$$

TABLE 2

| Material | Acoustic Impedance (kg/m² · s) |
| --- | --- |
| PZT 5A | $34 \times 10^6$ |
| methane (1 atm, 20 C) | 300 |
| matching layer (ideal) | $1 \times 10^5$ |

This typically requires a matching layer composed of a solid material with very low speed of sound and low density. However, in general suitable materials do not occur naturally and have to be constructed with special manufacturing processes. For example, suspensions of hollow glass microspheres in epoxy resin are used in the current Sensus transducer, matching layers using glass and resin microspheres are discussed, for example, in U.S. Pat. No. 4,523,122 and a matching layer using a dry gel material is discussed in, for example, U.S. Pat. No. 6,989,625, the disclosures of which are incorporated herein by reference as if set forth in their entirety.

The acoustic matching layer may include, for example, Polyethersulfone, Polypropylene, PTFE, PVDF, Nylon, Polyamide, PMMA, Vinylic/acrylic copolymer, Cellulose ester, Cellulose acetate, Nitrocellulose, and the like. Embodiments of the present inventive concept may use any acoustic matching layers without departing from the scope of the present inventive concept.

Figure 6:
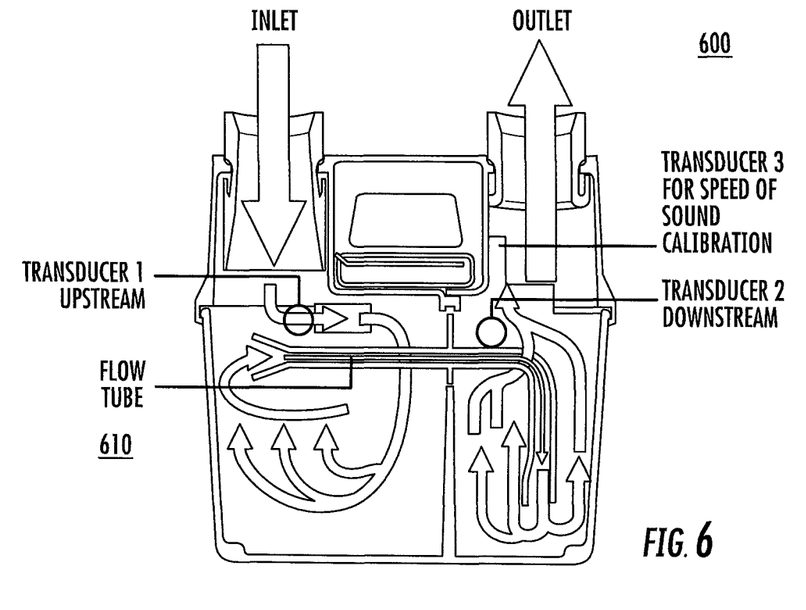
FIG. 6 is a block diagram illustrating an example gas meter including transducers in accordance with embodiments of the present inventive concept.

Transducers in accordance with embodiments discussed herein may be used in any device which lends itself to such transducer. For example, these transducers may be used in water meters, gas meters and the like. By way of example, transducers may be used in gas meters as illustrated in FIG. 6. As illustrated therein, the gas meter 600 includes three transducers. Transducer 1 (upstream) and transducer 2 (downstream) may be used to measure time-of-flight of an ultrasonic signal along the flow tube 610 in forward and reverse directions. The gas meter 600 may also be configured to compensate for gas properties and conditions using a separate sound measurement using transducer 3.

It will be understood that FIG. 6 is provided for example only and embodiments of the present inventive concept are not limited to this configuration. Transducers as discussed herein may be used in many different devices without departing from the scope of the present inventive concept.

It will be understood that embodiments of the present inventive concept illustrated in FIG. 1 may be fabricated using any methods know to those having skill in the art without departing from the scope of the present inventive concept. For example, the piezoelectric block may be manufactured or obtained from third party. In some embodiments, the piezoelectric materials may be soft PZT, grades P5A and P5H or substantial equivalents thereof; but as discussed above, the piezoelectric materials are not limited to PZT. The conductive flexible support layers may be bonded to the piezoelectric block using an adhesive to provide an electrical connection, rather than a soldered wire. The adhesive may be, for example, a two-part epoxy resin. The bonded structure may then be cured under heat and pressure in a chamber, for example, a mechanical alignment jig. The quantity of applied adhesive and process conditions provide electrical contact between the piezoelectric electrodes and the flexible support layers, allowing electrical connection to be made to the metal parts and avoiding the need for a solder contact with the piezoelectric block. It will be understood that the manufacturing process is not limited to the process discussed herein and, in fact, more cost-effective manufacturing routes would likely be used for mass production without departing from the scope of the present inventive concept.

As briefly discussed above with respect to FIGS. 1 through 7, some embodiments of the present inventive concept provide transducers that include upper and lower electrically conductive flexible support layers which provide mechanical protection, mounting and electrical contact, and optionally gas or liquid sealing functions. A matching layer as discussed above may be applied to the gas- or liquid-facing side of one of these sheets.

Example embodiments are described above with reference to block diagrams and/or flowchart illustrations of systems and devices. The functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A transducer comprising:
a single piezoelectric block having first and second opposing surfaces;
a first electrically conductive flexible support layer on the first surface of the piezoelectric block, the first electrically conductive flexible support layer having a first thickness; and
a second electrically conductive flexible support layer on the second surface of the piezoelectric block, the second electrically conductive flexible support layer having a second thickness,
wherein the first and second electrically conductive flexible support layers have a similar size and shape and overhang the first and second opposing surfaces of the single piezoelectric block, respectively, a substantially same distance on both sides of the single piezoelectric block.

2. The transducer of claim 1, wherein the first and second thicknesses are substantially the same and wherein the first and second thicknesses are substantially less than a thickness of the piezoelectric block.

3. The transducer of claim 1, wherein the first and second electrically conductive flexible support layers comprise thin metal sheets of material directly on the first and second opposing surfaces of the single piezoelectric block, respectively.

4. The transducer of claim 3, wherein the thin metal sheets of material comprise only stainless steel sheets of material.

5. The transducer of claim 1, wherein the first and second electrically conductive flexible support layers comprise flexible circuits with a copper trace.

6. The transducer of claim 1, wherein the first and second electrically conductive flexible support layers have a thickness of from about 0.025 mm to about 0.1 mm.

7. The transducer of claim 1, wherein the piezoelectric block comprises a soft PZT material selected from one of grade P5A material and P5H material.

8. The transducer of claim 1, wherein the piezoelectric block has a thickness of from about 0.5 mm to about 5.0 mm.

9. The transducer of claim 1, wherein a resonant frequency of the transducer is about 400 kHz and dimensions of the first and second electrically conductive flexible support layers are 4.2×4.2×0.1 mm; and dimensions of the piezoelectric block are 4×4×2 mm.

10. The transducer of claim 1, wherein the first and second electrically conductive flexible support layers are coupled to the first and second surfaces of the piezoelectric block, respectively, using an adhesive.

11. The transducer of claim 10, wherein electrical contact between the piezoelectric block and the first and second electrically conductive flexible support layers is obtained using the adhesive and without a wire soldered between the piezoelectric block and the first and second electrically conductive flexible support layers.

12. The transducer of claim 1, further comprising an acoustic matching layer on one of a gas and liquid facing surface of one of the first and second electrically conductive flexible support layers.

13. The transducer of claim 1, wherein the transducer is an ultrasonic transducer configured for one of a gas meter and a water meter.

14. A meter, comprising:
at least one transducer, the at least one transducer comprising:
a single piezoelectric block having first and second opposing surfaces;
a first conductive flexible support layer on the first surface of the piezoelectric block, the first conductive flexible support layer having a first thickness; and
a second electrically conductive flexible support layer on the second surface of the piezoelectric block, the second electrically conductive flexible support layer having a second thickness,
wherein the first and second electrically conductive flexible support layers have a similar size and shape and overhang the first and second surfaces of the single piezoelectric block, respectively, a substantially same distance on both sides of the single piezoelectric block.

15. The meter of claim 14, wherein the first and second thicknesses are substantially the same and wherein the first and second thicknesses are substantially less than a thickness of the piezoelectric block.

16. The meter of claim 14, wherein the first and second electrically conductive flexible support layers comprise thin metal sheets of material directly on the first and second opposing surfaces of the single piezoelectric block, respectively.

17. The meter of claim 16, wherein the thin metal sheets of material comprise only stainless steel sheets of material.

18. The meter of claim 14, wherein the first and second electrically conductive flexible support layers comprise flexible circuits with a copper trace.

19. The meter of claim 14, wherein the first and second electrically conductive flexible support layers have a thickness of from about 0.025 mm to about 0.1 mm.

20. The meter of claim 14, wherein the piezoelectric block comprises a soft piezoelectric material selected from one of grade P5A material and P5H material.

21. The meter of claim 14, wherein the piezoelectric block has a thickness of from about 0.5 mm to about 5.0 mm.

22. The meter of claim 14, further comprising an acoustic matching layer on one of a gas and a liquid facing surface of one of the first and second electrically conductive flexible support layers.

23. The meter of claim 14, wherein the at least one transducer comprises a plurality of transducers and are configured for one of a gas meter, a water meter and a heat meter.

* * * * *